United States Patent [19]
Gray et al.

[11] Patent Number: 5,492,933
[45] Date of Patent: Feb. 20, 1996

[54] METHODS AND COMPOSITIONS FOR TREATING URINARY INCONTINENCE AND OTHER DISORDERS USING OPTICALLY PURE R-TERODILINE AND HYDROXYLATED DERIVATIVES THEREOF

[75] Inventors: Nancy M. Gray, Marlboro, Mass.; James W. Young, Palo Alto, Calif.

[73] Assignee: Sepracor, Inc., Marlborough, Mass.

[21] Appl. No.: 134,271

[22] Filed: Oct. 8, 1993

[51] Int. Cl.$^6$ ................................................ A61K 31/135
[52] U.S. Cl. ............................................ 514/648; 514/646
[58] Field of Search ..................................... 514/648, 646

[56] References Cited

U.S. PATENT DOCUMENTS

| | | |
|---|---|---|
| 3,371,014 | 2/1968 | Carlsson . |
| 4,851,404 | 7/1989 | Ohnishi et al. ........................... 514/211 |
| 4,988,730 | 1/1991 | Kurbinits et al. ......................... 514/648 |

FOREIGN PATENT DOCUMENTS

| | | |
|---|---|---|
| 0427904 | 5/1991 | European Pat. Off. . |

OTHER PUBLICATIONS

Langtry and McTavish, et al "Terodiline, A review of its pharmological properties and therapeutic use" *Drugs*, vol. 40, No. 5, pp. 748–761. 1990.

Castenfors, et al, "Pilot Study of the effect of terodiline on obstruction Pulmonary disease", European Journal of Pharmocology, vol 8, pp. 197–201. 1975.

Noronha–Blob et al., "(+)–Terodiline: an $M_1$–selective muscarinic receptor antagonist. In vivo effects at muscarinic receptors mediating urinary bladder contraction, mydriasis and salivary secretion", *European Journal of Pahrmacology* 201: 135–142 (1991).

Bogentoft et al., "Worldwide safety profile of terodiline", Supplement to Urology 36(4): 58–62 (1990).

Enquist and Hermansson, "Separation of the enantiomers of β–receptor blocking agents and other cationic drugs using a CHIRAL–AGP column", J. Chromat. 519: 285–298 (1990).

Noren et al., "Biotransformation of terodiline v. stereoselectivity in hydroxylation by human liver microsomes", Chem.–Biol. Interactions 71: 325–337 (1989).

Andersson et al., "Actions of terodiline, its isomers and main metabolite on isolated detrusor muscle from rabbit and man", Pharmacology & Toxicology 63: 390–395 (1988).

Helander et al., "The stereochemistry of N–tert–butyl–4–(4–hydroxyphenyl)–4–phenyl–2–butylamines", Acta Pharmaceutica Scandinavica B 42: 35–38 (1988).

Noren et al., "Biotransformation of terodiline. IV. Identification of unconjugated metabolites in dog and human urine", Acta Pharmaceutica Suecica 25(6): 281–292 (1988).

Lindeke et al., "Biotransformation of terodiline. III. Opposed stereoselectivity in the benzylic and aromatic hydroxylations in rat liver microsomes", Xenobiotica 17(11): 1269–1278 (1987).

Andersson, "Clinical pharmacology of terodiline", Scand. J. Urol. Nephrol. Supp. 87: 13–20 (1984).

Fischer–Rasmussen, "Evaluation of long–term safety and clinical benfit of terodiline in women with urgency/urge incontinence. A multicenter study", Scand. J. Urol. Nephrol. Suppl. 87: 35–47 (1984).

Rud et al., "Terodiline inhibition of human bladder contraction. Effects in vitro and in women with unstable bladder", Acta Pharmacol. et Toxicol. 46(1): 31–38 (1980).

Vessman and Sundwall, "Identification of hydroxylated metabolites of terodiline in aminal and man", Acta Pharmacol. Toxicol. 28:89 (1970).

*Primary Examiner*—Raymond Henley, III
*Assistant Examiner*—Keith MacMillan
*Attorney, Agent, or Firm*—Heslin & Rothenberg

[57] ABSTRACT

Methods and compositions are disclosed utilizing the optically pure R-isomers of terodiline or of the hydroxylated derivatives of terodiline, These compounds are potent drugs for the treatment of urinary incontinence, obstructive pulmonary disease and such other conditions as are related to the compounds' activity as anticholinergic agents.

35 Claims, No Drawings

METHODS AND COMPOSITIONS FOR TREATING URINARY INCONTINENCE AND OTHER DISORDERS USING OPTICALLY PURE R-TERODILINE AND HYDROXYLATED DERIVATIVES THEREOF

1. BACKGROUND OF THE INVENTION

This invention relates to novel compositions of matter containing optically pure R-terodiline or a hydroxylated derivative of R-terodiline selected from the group consisting of 2R-N-tert-butyl-4 -(4-hydroxyphenyl)-4-phenyl-2-butylamine, R-N-tert-butyl-4,4-diphenyl-4-hydroxy-2-butylamine and R-N-(2 -hydroxymethyl-2-propyl)-4,4-diphenyl-2-butylamine. These compositions of matter possess potent activity in treating disorders such as urinary incontinence and obstructive pulmonary disease. Further, these compositions of matter possess potent activity in treating these disorders while substantially reducing the adverse effects including but not limited to cardiac arrhythmias, headache, dry mouth, constipation, heartburn, blurred vision, nausea, tremor, dizziness, confusion, rash, muscular weakness, sweating, insomnia, weight change and paralyticileus which are associated with the administration of the racemic mixture of terodiline.

Furthermore, the present invention encompasses methods for treating the above-identified conditions in a human by administering to a human in need of such therapy, optically pure or substantially optically pure R-terodiline, or an optically pure or substantially optically pure hydroxylated derivative of R-terodiline selected from the group consisting of 2R-N-tert-butyl-4-(4-hydroxyphenyl)-4-phenyl-2 -butylamine, R-N-(2-hydroxymethyl-2-propyl)-4,4 -diphenyl-2-butylamine, and R-N-tert-butyl-4,4 -diphenyl-4-hydroxy-2-butylamine.

1.1 STERIC RELATIONSHIP AND DRUG ACTION

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound. A compound prefixed with (−) or l is levorotatory and a compound prefixed with (+) or d is dextrorotatory. For a given chemical structure, these compounds, called stereoisomers, are identical except that they are mirror images of one another. Such a stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the β-adrenergic blocking agent, propranolol, which is known to be 100 times more potent than the D-enantiomer.

Furthermore, optical purity is important since certain isomers may actually be deleterious rather than simply inert. For example, the D-enantiomer of thalidomide is a safe and effective sedative when prescribed for the control of morning sickness during pregnancy, while the corresponding L-enantiomer has been thought to be a potent teratogen.

1.2 PHARMACODYNAMICS

The active compounds of the present compositions and methods include the optically pure R-isomers of the compound terodiline and of the optically pure hydroxylated derivatives of terodiline, selected from the group consisting of 2R-N-tert-butyl-4-(4-hydroxyphenyl)-4-phenyl-2-butylamine, R-N-tert-butyl- 4,4-diphenyl-4-hydroxy-2-butylamine and R-N-(2 -hydroxymethyl-2-propyl)-4,4-diphenyl-2-butylamine. Racemic terodiline is disclosed in U.S. Pat. No. 3,371,014. The metabolites or derivatives as well as the enantiomers of racemic terodiline are described, for example, in Noren et al., *Chem. Biol. Interact.*, 71:325–327 (1989) and European Patent Application No. 0 427 904 A1.

Chemically, the optical isomer of terodiline which is part of the present invention is R-N-tert-butyl- 4,4-diphenyl-2-butylamine or R-N-tert-butyl-1 -methyl-3,3-diphenylpropylamine. See the Merck Index 11th Edition, Monograph 9098 for the various chemical names for racemic terodiline. The structure of terodiline is shown below.

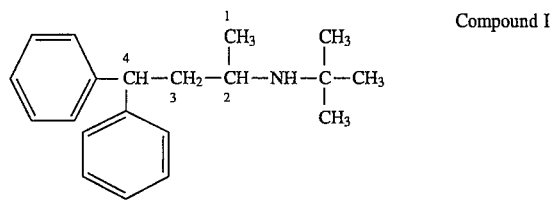

Compound I

It should be noted that certain derivatives of terodiline have two chiral centers, i.e., one at carbon 2 and one at carbon 4 (see Compound I above). There are four possible isomers for a compound having two chiral centers: (R,R), (S,S), (R,S) and (S,R). Of these, (R,R) and (S,S) are an example of a pair of enantiomers and (S,S) and (R,S) are an example of a pair of diastereoisomers. In accordance with the present invention, it has been found that the absolute configuration at the carbon 2 position has more pharmacological consequences. Thus, as used herein, the term "2R-N-tert-butyl-4-(4-hydroxyphenyl)-4 -phenyl-2-butylamine" is meant to include both diastereoisomers 2R,4S-N-tert-butyl-4-(4 -hydroxyphenyl)-4-phenyl-2-butylamine and 2R,4R-N-tert-butyl-4 -(4-hydroxyphenyl)-4-phenyl-2-butylamine, i.e., compounds where the absolute configuration at the carbon 2 position is R. These compounds, as well as R-N-tert-butyl-4,4-diphenyl-4-hydroxy-2-butylamine and R-N-(2-hydroxymethyl-2-propyl)-4,4-diphenyl-2-butylamine, will be collectively referred to herein as "hydroxylated derivatives of terodiline."

Lindeeke et al., *Xenobiotica*, 17:1269–1278 (1987) and Noren et al., *Chem. Biol. Interact.*, 71:325–327 (1989) describe the differences in the hydroxylation rates and patterns during metabolism of the two enantiomers of terodiline by human and rat liver microsomes. In addition, the enantiomers of terodiline are disclosed in Andersson et al., *Pharmacol. Toxicol.*, 63:390–395 (1988), and Larsson-Backström et al., *Acta Pharmacol. et Toxicol.* 57:8–17 (1985). These references conclude that the R-isomer contributes to a main part of terodiline's effect on the bladder detrusor muscle. However, Larsson-Backström et al., *Acta Pharmacol. Toxicol.*, 57:8–17 (1985) summarizes the effects of the two enantiomers of terodiline on vascular tissue. This reference concludes that the S-isomer is the more potent calcium antagonist. Additionally, Noronha-Blob et al., *Eur. J. Pharmacol.*, 201:135–142 (1991) allege that the treatment of bladder disorders may be more related to non-cholinergic actions of terodiline. Thus, there is no clear teaching in the art as to which of the two enantiomers is the more active and/or more useful for treating disorders associated with the compound's pharmacology profile. Further, there is no teaching in the art as to which, if any, of the hydroxylated derivatives of terodiline are therapeutically or prophylactically useful in humans. Moreover, there is no teaching or suggestion with regard to the usefulness in humans of the optically pure hydroxylated derivatives R-terodiline.

Terodiline has been administered as a hydrochloride salt; however, terodiline is no longer commercially available. The hydroxylated derivatives described herein are also not available commercially, either as racemates or as optically pure compounds.

The racemic mixture of terodiline was used primarily as an agent to treat urinary incontinence. The detrusor muscle, which provides the propulsive force for emptying the bladder, consists of interlacing fibers of smooth muscle that are under control by pelvic nerves from the spinal cord. Contractions of the detrusor muscle are synergistic and are stimulated by both acetyl choline and calcium. Involuntary contraction of the detrusor muscle is the cause of urinary incontinence; therefore, agents which block the actions of acetyl choline or calcium on the detrusor muscle serve as therapeutic agents for the treatment of urinary incontinence. In vitro studies show that the racemic mixture of terodiline possesses anticholinergic activity and inhibits carbachol-induced muscle contractions. The racemic mixture of terodiline also showed specific calcium antagonism in the bladder. The local anaesthetic and spasmolytic activities of racemic terodiline may also contribute to its activity. See Langtry et al., *Drugs*, 40(5):748–761 (1990); Bogentoft et al., *Supplement to Urology*, Vol. XXXVI, 4:58–62 (1990); Andersson, *Scand. J. Urol. Nephrol. Supp.*, 87:13–20 (1984).

Further, the racemic mixture of terodiline can be useful for treating obstructive pulmonary disease. Because of its activity as an anticholinergic agent, terodiline is responsible for decreases in the volume of bronchial secretion and thereby alleviates the obstruction of airflow in the lungs. See Castenfors et al., *Eur. J. Clin. Pharmacol.*, 8:197–200 (1975).

While the racemic mixture of terodiline has the foregoing advantages, it also has disadvantages, such as causing adverse effects, including but not limited to cardiac arrhythmias (especially torsades de pointes), headache, dry mouth, constipation, heartburn, blurred vision, tremor, nausea, dizziness, confusion, rash, muscular weakness, sweating, insomnia, weight change and paralytic ileus. Thus, it would be desirable to find a compound with the advantages of racemic terodiline which would not have the aforementioned disadvantages.

2. SUMMARY OF THE INVENTION

It has now been discovered that the optically pure R-isomers of terodiline, and of the hydroxylated derivatives of terodiline, are effective agents for treating disorders in a human, such as urinary incontinence and obstructive pulmonary disease.

The invention encompasses novel compositions of matter containing optically pure R-terodiline or a hydroxylated derivative thereof as the active ingredient. These compositions of matter are effective for treating urinary incontinence while substantially reducing adverse effects including but not limited to cardiac arrhythmias, headache, dry mouth, constipation, heartburn, blurred vision, tremor, dizziness, confusion, rash, and muscular weakness, sweating, insomnia, weight change and paralytic ileus which are associated with the administration of the racemic mixture of terodiline.

Moreover, the novel compositions of matter containing R-terodiline, or one of the hydroxylated derivatives thereof, are useful for treating obstructive pulmonary disease while substantially reducing adverse effects associated with the administration of racemic terodiline.

The present invention also encompasses methods for treating the above-described disorders in a human while substantially reducing adverse effects associated with the administration of racemic terodiline, comprising administering an effective amount of the optically pure R-isomer of terodiline to a human. The present invention also encompasses methods for treating the above-described conditions in a human, comprising administering an effective amount of the optically pure R-isomer of a hydroxylated derivative of terodiline to a human.

3. DETAILED DESCRIPTION OF THE INVENTION

The present invention encompasses a method of treating urinary incontinence in a human while substantially reducing the adverse effects associated with the administration of racemic terodiline, which comprises administering to a human in need of such therapy an effective amount of R-terodiline, or a pharmaceutically acceptable salt thereof, substantially free of its S-stereoisomer, said effective amount being sufficient to alleviate urinary incontinence but insufficient to cause adverse effects associated with racemic terodiline.

The invention also encompasses a method for treating urinary incontinence in a human while substantially reducing adverse effects associated with the administration of racemic terodiline, which comprises administering to a human in need of such therapy an effective amount of a compound selected from the group consisting of 2R-N-tert-butyl-4-(4-hydroxyphenyl)-4-phenyl-2-butylamine, R-N-(2-hydroxymethyl-2-propyl)-4,4-diphenyl-2-butylamine, and R-N-tert-butyl-4,4-diphenyl-4-hydroxy-2-butylamine or a pharmaceutically acceptable salt thereof, substantially free of the 2S-stereoisomer, said effective amount being sufficient to alleviate urinary incontinence but insufficient to cause adverse effects associated with the administration of racemic terodiline.

The present invention further includes a method of treating urinary incontinence in a human comprising administering to a human in need of such therapy an effective amount of a compound selected from the group consisting of 2R-N-tert-butyl-4-(4-hydroxyphenyl)-4-phenyl-2-butylamine, R-N-tert-butyl-4,4-diphenyl-4-hydroxy-2-butylamine and R-N-(2-hydroxymethyl-2-propyl)-4,4-diphenyl-2-butylamine, or pharmaceutically acceptable salts thereof, substantially free of its 2S-stereoisomer, said effective amount being sufficient to alleviate urinary incontinence.

The present invention also encompasses a pharmaceutical composition for the treatment of urinary incontinence in a human, which comprises an effective amount of a compound selected from the group consisting of R-terodiline, 2R-N-tert-butyl-4-(4-hydroxyphenyl)-4-phenyl-2-butylamine, R-N-tert-butyl-4,4-diphenyl-4-hydroxy-2-butylamine, and R-N-(2-hydroxymethyl-2-propyl)-4,4-diphenyl-2-butylamine or pharmaceutically acceptable salts thereof, wherein said compound is substantially free of its 2S-stereoisomer, said effective amount being sufficient to alleviate urinary incontinence but insufficient to cause adverse effects associated with the administration of racemic terodiline; and a pharmaceutically acceptable carrier.

In addition, the present invention encompasses a method of treating obstructive pulmonary disease in a human while substantially reducing adverse effects associated with the administration of racemic terodiline, comprising administering to a human in need of such therapy an effective amount of R-terodiline, or a pharmaceutically acceptable salt thereof, substantially free of its S-stereoisomer, said effective amount being sufficient to alleviate obstructive pulmonary disease but insufficient to cause adverse effects associated with the administration of racemic terodiline.

The present invention also encompasses a method of treating obstructive pulmonary disease in a human while substantially reducing adverse effects associated with the administration of racemic terodiline, comprising administering to a human in need of such therapy an effective amount of a compound selected from the group consisting of 2R-N-tert-butyl-4-(4-hydroxyphenyl)-4-phenyl-2-butylamine, R-N-tert-butyl- 4,4-diphenyl-4-hydroxy-2-butylamine and R-N-(2-hydroxymethyl-2-propyl)-4,4-diphenyl-2-butylamine, or a pharmaceutically acceptable salt thereof, substantially free of its 2R-stereoisomer, said effective amount being sufficient to alleviate obstructive pulmonary disease but insufficient to cause adverse effects associated with the administration of racemic terodiline.

The present invention further encompasses a method of treating obstructive pulmonary disease in a human comprising administering to a human in need of such therapy an effective amount of a compound selected from the group consisting of 2R-N-tert-butyl- 4-(4-hydroxyphenyl)-4-phenyl-2-butylamine, R-N-tert-butyl- 4,4-diphenyl-4-hydroxy-2-butylamine and R-N-(2-hydroxymethyl-2-propyl)-4,4-diphenyl-2-butylamine, or pharmaceutically acceptable salts thereof, substantially free of its 2S-stereoisomer, said effective amount being sufficient to alleviate obstructive pulmonary disease.

Also, the present invention encompasses a pharmaceutical composition for the treatment of obstructive pulmonary disease in a human, which comprises an effective amount of a compound selected from the group consisting of R-terodiline, 2R-N-tert-butyl- 4-(4-hydroxyphenyl)-4-phenyl-2-butylamine, R-N-tert-butyl- 4,4-diphenyl-4-hydroxy-2-butylamine, and R-N-( 2-hydroxymethyl-2-propyl)-4,4-diphenyl-2-butylamine, or pharmaceutically acceptable salts thereof, wherein said compound is substantially free of its 2S-stereoisomer, said effective amount being sufficient to alleviate obstructive pulmonary disease but insufficient to cause adverse effects of racemic terodiline; and a pharmaceutically acceptable carrier.

The racemic mixture of terodiline (e.g., a 1:1 racemic mixture of the R- and S-enantiomers) exhibits anticholinergic and calcium antagonist activity, and provides therapy and/or a reduction of symptoms in a variety of conditions and disorders; however, the racemic mixture, while offering the expectation of efficacy, causes adverse effects. Utilizing the optically pure or substantially optically pure R-isomer of terodiline or of a hydroxylated derivative of terodiline, results in clearer dose related definitions of efficacy, diminished adverse effects, and accordingly, an improved therapeutic index. It is therefore more desirable to use the R-isomer of terodiline or of one of the hydroxylated derivatives of terodiline than to use racemic terodiline.

The term "adverse effects" as used herein includes, but is not limited to cardiac arrhythmias, headache, dry mouth, constipation, heartburn, blurred vision, nausea, tremor, dizziness, confusion, rash, muscular weakness, sweating, insomnia, weight change, and paralytic ileus. The term "cardiac arrhythmias" includes, but is not limited to ventricular tachyarrhythmias, torsades de pointes and ventricular fibrillation.

The terms "substantially free of its S-stereoisomer" and "substantially free of its 2S-stereoisomer" as used herein, relates to the proportion of the R-isomer of terodiline to that of the S-isomer, or relates to the proportion of the 2R-isomer of the hydroxylated derivative in relation to the 2S-isomer thereof. It should be noted, as mentioned above, that the 2R-isomer is meant to include both diastereoisomers of the compounds with two chiral centers, i.e., the two compounds with the absolute configuration being R at the carbon 2 position, e.g., (2R, 4S) and (2R, 4R).

In a preferred embodiment, the term "substantially free of its S-stereoisomer" or "substantially free of its 2S-stereoisomer" as used herein means that the composition contains at least 90% by weight of R-isomer and 10% by weight or less of the S-isomer. In the most preferred embodiment, the terms "substantially free of the S-stereoisomer" or "substantially free of its 2S-stereoisomer" mean that the composition contains at least 99% by weight of the R-isomer and 1% or less of the S-isomer. In another preferred embodiment, the terms "substantially free of its S-stereoisomer" or "substantially free of its 2S-stereoisomer" as used herein mean that the composition contains greater than 99% by weight of the R-isomer. The above percentages are based on the total amount of terodiline or of the hydroxylated derivative of terodiline present in the composition.

The terms "optically pure or substantially optically pure R-isomer of terodiline" and "optically pure or substantially optically pure hydroxylated derivatives of terodiline" are also encompassed by the above-described amounts.

The term "a method of treating urinary incontinence" as used herein means the treatment of premature urination due to conditions including, but not limited to, neurogenic bladder dysfunction, nocturnal enuresis, irritative bladder, chronic cystitis or prostatitis, psychosomatic bladder, nervous pollakiuria, and stress or motor urge incontinence.

The term "a method of treating obstructive pulmonary disease" as used herein means the treatment of bronchial obstruction due to conditions such as bronchial asthma, bronchitis or emphysema.

The separation of the enantiomeric pairs of terodiline metabolites and preparation of the enantiomers of terodiline is disclosed in Enquist et al., *J. Chromatog.*, 519:285–298 (1990), Helander et al., *Acta Chem. Scand. Ser. B Org. Chem. Biochem.*, 42:35–38 (1988) and European Patent Application EP 0 427 904 A1, the disclosures of which are incorporated herein by reference. These references describe the separation of the enantiomers by crystallization and reversed phase liquid chromatography. In addition, the optically pure R-isomers of terodiline and of the hydroxylated derivatives of terodiline can be obtained by the reduction of an intermediate imine by employing optically pure chiral reducing agents as shown in the following Scheme I:

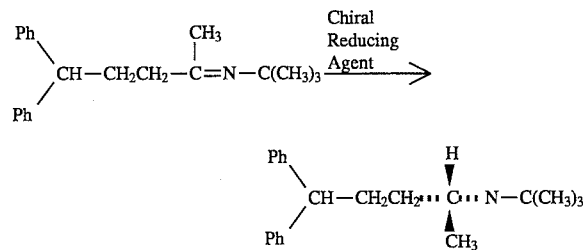

Examples of such chiral reducing agents are (+)beta-chlorodiisopinocamphenylborane, (−)beta-chlorodiisopinocamphenylborane, R,R,-N,N'-bis(mono-isopinocamphenylborane)-N,N,N',N'-tetramethylenediamine or other such reagents familiar to those skilled in the art.

The magnitude of a prophylactic or therapeutic dose of the R-isomers of terodiline or of the hydroxylated derivatives of terodiline in the acute or chronic management of disease will vary with the severity of the condition to be treated, and the route of administration. The dose, and perhaps the dose frequency, will also vary according to the age, body weight, response, and past medical history of the individual patient. In general, the recommended daily dose ranges, for the conditions described herein, lie within the range of from about 5 mg to about 100 mg per day given as a once daily administration or in divided doses, if required. Preferably, a daily dose range should be between about 10 mg to about 75 mg per day, given as a once daily administration or in divided doses, if required; and most preferably, a daily dose range should be between about 10 mg to about 50 mg per day, given as a once daily administration or in divided doses, if required. In managing the patient, the therapy should be initiated at a lower dose, perhaps about 15 mg to about 25 mg and increased if necessary up to about 50 mg or higher depending on the patient's global response. It is further recommend that children, and patients aged over 65 years, and those with impaired renal or hepatic function, initially receive low doses, and that they be titrated based on global response and blood level. It may be necessary to use dosages outside these ranges in some cases. It is noted that the physician will know when to adjust, interrupt or terminate the treatment regimen of a particular individual according to that individual's condition and response.

The various terms "an amount being sufficient to alleviate said urinary incontinence but insufficient to cause adverse effects" and "an amount being sufficient to alleviate obstructive pulmonary disease but insufficient to cause adverse effects" are encompassed by the above described dosage amounts and dose frequency schedule.

The pharmaceutical compositions of the present invention contain the R-isomers of terodiline or of the hydroxylated derivatives of terodiline, selected from the group consisting of 2R-N-tert-butyl-4-(4-hydroxyphenyl)-4-phenyl-2-butylamine, R-N-tert-butyl- 4,4-diphenyl-4-hydroxy-2-butylamine, and R-N-(2 -hydroxymethyl-2-propyl)-4,4-diphenyl-2-butylamine as active ingredients, or pharmaceutically acceptable salts thereof, and may also contain a pharmaceutically acceptable carrier and, optionally, other therapeutic ingredients known to those skilled in the art.

Since the compound of the present invention is basic, the term "pharmaceutically acceptable salts" refers to salts prepared from pharmaceutically acceptable non-toxic acids including inorganic acids and organic acids. Such acids include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pyemic, pantothenic, phosphoric, succinic, sulfuric, tartaric, p-toluenesulfonic, and the like. Particularly preferred are besylate, hydrobromic, hydrochloric, phosphoric and sulfuric acids.

Any suitable route of administration may be employed for providing the patient with an effective dosage of the R-isomers of terodiline or of the hydroxylated derivatives of terodiline. For example, oral, rectal, parenteral (e.g., intravenous or intramuscular), transdermal, subcutaneous, topical, and the like may be employed. Dosage forms include tablets, troches, dispersions, suspensions, solutions, capsules, patches, creams, aerosols and the like. The most preferred route of the present invention is the oral route. The compositions may be conveniently presented in unit dosage form, and prepared by any of the methods well known in the art of pharmacy.

In the case where an oral composition is employed, a suitable dosage range for use is from about 5 mg to about 100 mg total daily dose, given as a once daily administration or in divided doses if required. Preferably, a dose range of from about 10 mg to about 75 mg is given as a once daily administration or in divided doses if required, and most preferably a dose range of from about 10 mg to about 50 mg is given as a once daily administration or in divided doses if required. Patients should be upwardly titrated from below to within this dose range to a satisfactory control of symptoms or blood pressure, as appropriate.

In practical use, the R-isomers of terodiline or of the hydroxylated derivatives of terodiline can be combined as the active ingredient in intimate admixture with a pharmaceutical carrier according to conventional pharmaceutical compounding techniques. The carrier may take a wide variety of forms depending on the form of the preparation desired for administration, e.g., oral or parenteral (including intravenous injections or infusions). In preparing the compositions for oral dosage form, any of the usual pharmaceutical media may be employed, such as carriers. In the case of oral liquid preparations (for example, suspensions, solutions, and elixirs) or aerosols, suitable carriers include water, glycols, oils, alcohols, flavoring agents, preservatives, coloring agents, and the like. In the case of oral solid preparations (for example, powders, capsules, and tablets), suitable carriers include starches, sugars, microcrystalline cellulose, diluents, granulating agents, lubricants, binders, disintegrating agents and the like. Oral solid preparations are preferred over oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; 3,632,200; 4,008,719, 4,687,660; 4,769,027, the disclosures of which are incorporated herein by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such pharmaceutical compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, and/or surface active or dispersing agent. Molded tablets may be made by molding, in a suitable machine, a mixture of the powdered compound moistened with an inert liquid diluent.

It is preferred that each tablet contain from about 5 mg to about 100 mg of the active ingredient, and each cachet or capsule contain from about 5 mg to about 100 mg of the active ingredient, the R-isomers of terodiline or of the hydroxylated derivatives of terodiline. Most preferably, the tablet, cachet or capsule contains either one of three dosages, e.g. about 15 mg, about 25 mg and about 50 mg of the active ingredient.

The invention is further defined by reference to the following examples describing in detail the preparation of the compositions of the present invention, as well as their utility. It will be apparent to those skilled in the art that many modifications, both to materials and methods, may be practiced without departing from the purpose and interest of this invention.

All temperatures are in degrees Celsius.

4. EXAMPLES

4.1 Example 1

The potential for promoting arrhythmia is evaluated by examining the effects of the optically pure isomers of terodiline and of the hydroxylated derivatives thereof on cardiac action potential and contractility in human and canine hearts.

Torsades de pointes is a well known side effect of antiarrhythmic drugs, such as quinidine, sotalol and acetylprocainamide, which cause a prolongation of cardiac repolarization. All of these drugs have in common the ability to block a cellular potassium channel called the delayed rectifier ($I_k$), and it is generally assumed that this is mechanistically linked to their ability to induce the syndrome of torsades de pointes. [See Zehender et al., *Cardiovascular Drugs Ther.*, 5:515–530 (1991).]

A. To determine the effects of racemic terodiline, the optically pure isomers of terodiline and the optically pure hydroxylated derivatives on QT duration and action potential duration in isolated guinea pig hearts, the hearts are perfused with an oxygenated Tyrode's solution, containing 0.0; 1.0; 5.0 or 10.0 μM of the test compound. QT duration and action potential duration (APD) are measured from cardiac electrodes. APD is measured at 50% (APD-50) and 90% (APD-90). The test compounds include racemic terodiline, R-terodiline, S-terodiline as well as the racemates, R- and S- isomers of the hydroxylated derivatives of terodiline: 2-N-tert-butyl-4-(4 -hydroxyphenyl)-4-phenyl-2-butylamine, N-tert-butyl-4,4-diphenyl-4-hydroxy-2-butylamine and N-(2 -hydroxymethyl-2-propyl)-4,4-diphenyl-2-butylamine. According to the studies of Zehender et al., these results are indicative of a potential arrhythmogenic effect of the test compounds in vivo.

B. To confirm this observation in human tissue in vitro, healthy right ventricular trabeculae are harvested from failing human hearts removed at the time of transplantation and are placed in tissue baths, designed for microelectrode impalement. Following an equilibration period, a thin trabeculum is impaled intracellularly, and the action potential is recorded. After equilibration, the test compounds at doses of $10^{-8}$ and $10^{-4}$M are added in cumulative fashion. Action potential duration is measured at 50% (APD-50) and/or 90% (APD-90) repolarization. In separate experiments, trabeculae are divided into 3 subgroups for each test compound, receiving either the R-isomer, S-isomer or racemate to determine the respective effects on contractility.

C. To confirm the observation in vivo, mongrel dogs of either sex weighing 5–20 kg are anesthetized and instrumented by standard techniques for blood pressure and EKG. A solid state transducer for dP/dT is placed in the left cardiac ventricle, and an epicardial electrode is put into place. The test compound is infused at progressively higher doses, beginning at 1 μg/kg/min for 15 minutes and increased incrementally until a cardiovascular collapse ensues. Parameters measured are: blood pressure, heart rate, dP/dT, and the QT-interval. Measurements of hemodynamics and electrical activity are made in response to each R-isomer, S-isomer and racemate.

4.2 EXAMPLE 2

ORAL FORMULATION

| Formula | Capsules: Quantity per capsule in mg. | | |
|---|---|---|---|
| Active ingredient | A | B | C |
| R-Terodiline | 15.0 | 25.0 | 50.0 |
| Starch 1500 | 84.0 | 74.0 | 49.0 |
| Magnesium Stearate | 1.0 | 1.0 | 1.0 |
| Compression Weight | 100.0 | 100.0 | 100.0 |

The active ingredient is sieved and blended with the excipients. The mixture is filled into suitably sized two-piece hard gelatin capsules using suitable machinery. Other doses may be prepared by altering the fill weight and if necessary, changing the capsule size to suit.

4.3 EXAMPLE 3

ORAL FORMULATION

| Formula | Tablets: Quantity per tablet in mg. | | |
|---|---|---|---|
| Active ingredient | A | B | C |
| R-Terodiline | 15.0 | 25.0 | 50.0 |
| Lactose BP | 139.0 | 129.0 | 104.0 |
| Starch BP | 30.0 | 30.0 | 30.0 |
| Pregelatinized Maize Starch BP | 15.0 | 15.0 | 15.0 |
| Magnesium Stearate BP | 1.0 | 1.0 | 1.0 |
| Compression Weight | 200.0 | 200.0 | 200.0 |

The active ingredient is sieved through a suitable sieve and blended with the lactose, starch, and pregelatinized maize starch. Suitable volumes of purified water are added and the powders are granulated. After drying, the granules are screened and blended with the magnesium stearate. The granules are compressed into tablets of desired shape, thickness, hardness, and disintegration. If desired, tablets may be coated by standard aqueous or nonaqueous techniques. Other doses may be prepared by altering the ratio of the active ingredient to the lactose, or by changing the compression weight and, if necessary, the size or shape of the tablet to suit.

What is claimed is:

1. A method of treating urinary incontinence in a human while substantially reducing adverse effects associated with the administration of racemic terodiline, comprising administering to said human a therapeutically effective amount of a compound selected from the group consisting of R-terodiline, 2R-N-tert-butyl-4-(4-hydroxyphenyl)-4-phenyl-2-butylamine, R-N-(2-hydroxymethyl-2-propyl)-4,4-diphenyl-2-butylamine, R-N-tert-butyl-4,4-diphenyl-4-hydroxy-2-butylamine, or pharmaceutically acceptable salts thereof, substantially free of the S-stereoisomer.

2. The method of claim 1 wherein the administration is by intravenous infusion, transdermal delivery, or orally as a tablet or a capsule.

3. The method of claim 2 wherein the amount administered is from about 5 mg to about 100 mg.

4. The method of claim 3 wherein the amount administered is from about 10 mg to about 75 mg.

5. The method of claim 4 wherein the amount administered is from about 10 mg to about 50 mg.

6. The method of claim 1 wherein the amount of R-terodiline, 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or a pharmaceutically acceptable salt thereof, is greater than approximately 90% by weight of the total amount of terodiline or hydroxylated derivative of terodiline.

7. The method of claim 2 wherein R-terodiline, 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof, is administered together with a pharmaceutically acceptable carrier.

8. The method according to claim 2 wherein R-terodiline, 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof, is administered as a hydrochloride salt.

9. A method of treating urinary incontinence in a human comprising administering to said human a therapeutically effective amount of a compound selected from the group consisting of 2R-N-tert-butyl-4-(4-hydroxyphenyl)-4-phenyl-2-butylamine, R-N-(2-hydroxymethyl-2-propyl)-4,4-diphenyl-2-butylamine, R-N-tert-butyl-4,4-diphenyl-4-hydroxy-2-butylamine, or pharmaceutically acceptable salts thereof, substantially free of the 2S-stereoisomer.

10. The method of claim 9 wherein the administration is by intravenous infusion, transdermal delivery, or orally as a tablet or a capsule.

11. The method of claim 10 wherein the amount administered is from about 5 mg to about 100 mg.

12. The method of claim 11 wherein the amount administered is from about 10 mg to about 75 mg.

13. The method of claim 12 wherein the amount administered is from about 10 mg to about 50 mg.

14. The method of claim 9 wherein the effective amount of 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or a pharmaceutically acceptable salt thereof, is greater than approximately 90% by weight of the total amount of hydroxylated derivative of terodiline.

15. The method of claim 10 wherein 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof, is administered together with a pharmaceutically acceptable carrier.

16. The method according to claim 10 wherein 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof, is administered as a hydrochloride salt.

17. A method of treating obstructive pulmonary disease in a human while substantially reducing adverse effects associated with the administration of racemic terodiline, comprising administering to said human a therapeutically effective amount of a compound selected from the group consisting of R-terodiline, 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof, substantially free of the S-stereoisomer.

18. The method of claim 17 wherein the administration is by intravenous infusion, transdermal delivery, orally as a tablet or a capsule or by aerosol inhalation.

19. The method of claim 18 wherein the amount administered is from about 5 mg to about 100 mg.

20. The method of claim 19 wherein the amount administered is from about 10 mg to about 75 mg.

21. The method of claim 20 wherein the amount administered is from about 10 mg to about 50 mg.

22. The method of claim 17 wherein said effective amount of R-terodiline, 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof is greater than 90% by weight of the total amount of terodiline or hydroxylated derivative of terodiline.

23. The method of claim 17 wherein R-terodiline, 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof, is administered together with a pharmaceutically acceptable carrier.

24. The method according to claim 18 wherein R-terodiline, 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof, is administered as a hydrochloride salt.

25. A method of treating obstructive pulmonary disease in a human comprising administering to said human a therapeutically effective amount of a compound selected from the group consisting of 2R-N-tert-butyl-4-(4-hydroxyphenyl)-4-phenyl-2-butylamine, R-N-tert-butyl-4,4-diphenyl-4-hydroxy-2-butylamine, and R-N-(2-hydroxymethyl-2-propyl)-4,4-diphenyl-2-butylamine, or pharmaceutically acceptable salts thereof, substantially free of the 2S-stereoisomer.

26. The method of claim 25 wherein the administration is by intravenous infusion, transdermal delivery, orally as a tablet or a capsule or by aerosol inhalation.

27. The method of claim 26 wherein the amount administered is from about 5 mg to about 100 mg.

28. The method of claim 27 wherein the amount administered is from about 10 mg to about 75 mg.

29. The method of claim 28 wherein the amount administered is from about 10 mg to about 50 mg.

30. The method of claim 25 wherein said effective amount of 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2- butylamine, or pharmaceutically acceptable salts thereof, is greater than 90% by weight of the total amount of the hydroxylated derivative of terodiline.

31. The method of claim 25 wherein 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4-diphenyl-2-butylamine, or pharmaceutically acceptable salts thereof, is administered together with a pharmaceutically acceptable carrier.

32. The method according to claim 26 wherein 2R-N-tert-butyl-4-(4-hydroxyphenyl)-4-phenyl-2-butylamine, R-N-tert-butyl-4,4-diphenyl-4-hydroxy-2-butylamine, R-N-(2-hydroxymethyl-2-propyl)-4,4 -diphenyl-2-butylamine or pharmaceutically acceptable salts thereof, is administered as a hydrochloride salt.

33. A pharmaceutical composition useful for the treatment of a disease selected from the group consisting of urinary incontinence and obstructive pulmonary disease, the composition comprising an effective amount of a compound selected from the group consisting of R-terodiline, 2R-N-tert-butyl- 4-(4-hydroxyphenyl)-4-phenyl-2-butylamine, R-N-tert-butyl- 4,4-diphenyl-4-hydroxy-2-butylamine, R-N-(2 -hydroxymethyl-2-propyl)-4,4-diphenyl-2-butylamine, and pharmaceutically acceptable salts thereof, wherein said pharmaceutical composition comprises, at least in part, said hydroxylated derivatives of R-terodiline substantially free of its S-stereoisomer; and a pharmaceutically acceptable carrier.

34. A pharmaceutical composition according to claim 18 wherein said composition is adapted for oral administration.

35. A pharmaceutical composition according to claim 33 adapted for intravenous delivery.

* * * * *